US00PP31385P2

(12) United States Plant Patent
Mathey

(10) Patent No.: US PP31,385 P2
(45) Date of Patent: Jan. 21, 2020

(54) ***LAGERSTROEMIA* PLANT NAMED 'SMNLIMG'**

(50) Latin Name: *Lagerstroemia indica*
Varietal Denomination: SMNLIMG

(71) Applicant: Megan M Mathey, Holland, MI (US)

(72) Inventor: Megan M Mathey, Holland, MI (US)

(73) Assignee: Spring Meadow Nursery, Inc., Spring Lake, MI (US)

( * ) Notice: Subject to any disclaimer, the term of this patent is extended or adjusted under 35 U.S.C. 154(b) by 0 days.

(21) Appl. No.: 16/350,937

(22) Filed: Jan. 31, 2019

(51) Int. Cl.
*A01H 5/02* (2018.01)
*A01H 6/00* (2018.01)

(52) U.S. Cl.
USPC ..... Plt./252
CPC ..... *A01H 6/00* (2018.05)

(58) Field of Classification Search
USPC ..... Plt./252
CPC ..... A01H 5/02
See application file for complete search history.

*Primary Examiner* — Kent L Bell
(74) *Attorney, Agent, or Firm* — Cassandra Bright

(57) ABSTRACT

A new and distinct *Lagerstroemia* cultivar named 'SMNLIMG' is disclosed, characterized by rich red flowers, and dark glossy foliage. Plants are compact and freely branching. The new variety is a *Lagerstroemia*, normally used for outdoor ornamental purposes.

3 Drawing Sheets

Latin name of the genus and species: *Lagerstroemia indica.*

Variety denomination: 'SMNLIMG'.

BACKGROUND OF THE INVENTION

The new *Lagerstroemia* cultivar is a product of a planned breeding program conducted by the inventor, Megan Mathey, in Grand Haven, Mich. The objective of the breeding program was to develop new foliage colors, and more compact habits. The open pollination resulting in this new variety was made during July of 2013.

The seed parent is the commercial variety referred to as *Lagerstroemia* 'Coral Magic', U.S. Plant Pat. No. 23,922. The pollen parent is unidentified. The new variety was selected in July of 2015 by the inventor in a group of seedlings resulting from the 2013 open pollination, in a nursery in Grand Haven, Mich.

Asexual reproduction of the new cultivar was performed by softwood cuttings. This was first performed at the same nursery in Grand Haven, Mich. during July of 2015, and has shown that the unique features of this cultivar are stable and reproduced true to type in multiple successive generations.

SUMMARY OF THE INVENTION

The cultivar 'SMNLIMG' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMNLIMG' These characteristics in combination distinguish 'SMNLIMG' as a new and distinct *Lagerstroemia* cultivar:

1. Rich red flowers.
2. Dense, dwarf plant.
3. Glossy foliage.

4. Greyed-Red and Greyed-Purple new foliage, maturing to dark green.

PARENT COMPARISON

Plants of the new cultivar 'SMNLIMG' are similar to plants of the seed parent, *Lagerstroemia* 'Coral Magic', U.S. Plant Pat. No. 23,922, in most horticultural characteristics; however, plants of the new cultivar 'SMNLIMG' differ in the following;

1. The new variety has dark green mature foliage, while the seed parent has lighter green foliage.
2. The new variety has magenta colored flowers, while, the seed parent has coral flowers.

COMMERCIAL COMPARISON

Plants of the new cultivar 'SMNLIMG' are comparable to the commercial variety *Lagerstroemia* 'G2X133271', U.S. Plant Pat. No. 27,474. The two *Lagerstroemia* varieties are similar in most horticultural characteristics; however, the new variety 'SMNLIMG' differs in the following;

1. The new variety is dwarf, more compact; this comparator is a larger spreading plant.
2. New variety has green, greyed-red and greyed-purple foliage, this comparator has green foliage.
3. New variety has bright, red-pink pink flowers; comparator has darker red-pink flowers.

BRIEF DESCRIPTION OF THE PHOTOGRAPHS

The accompanying photograph in FIG. 1 illustrates in full color typical new foliage of 'SMNLIMG'.

Figure 1:
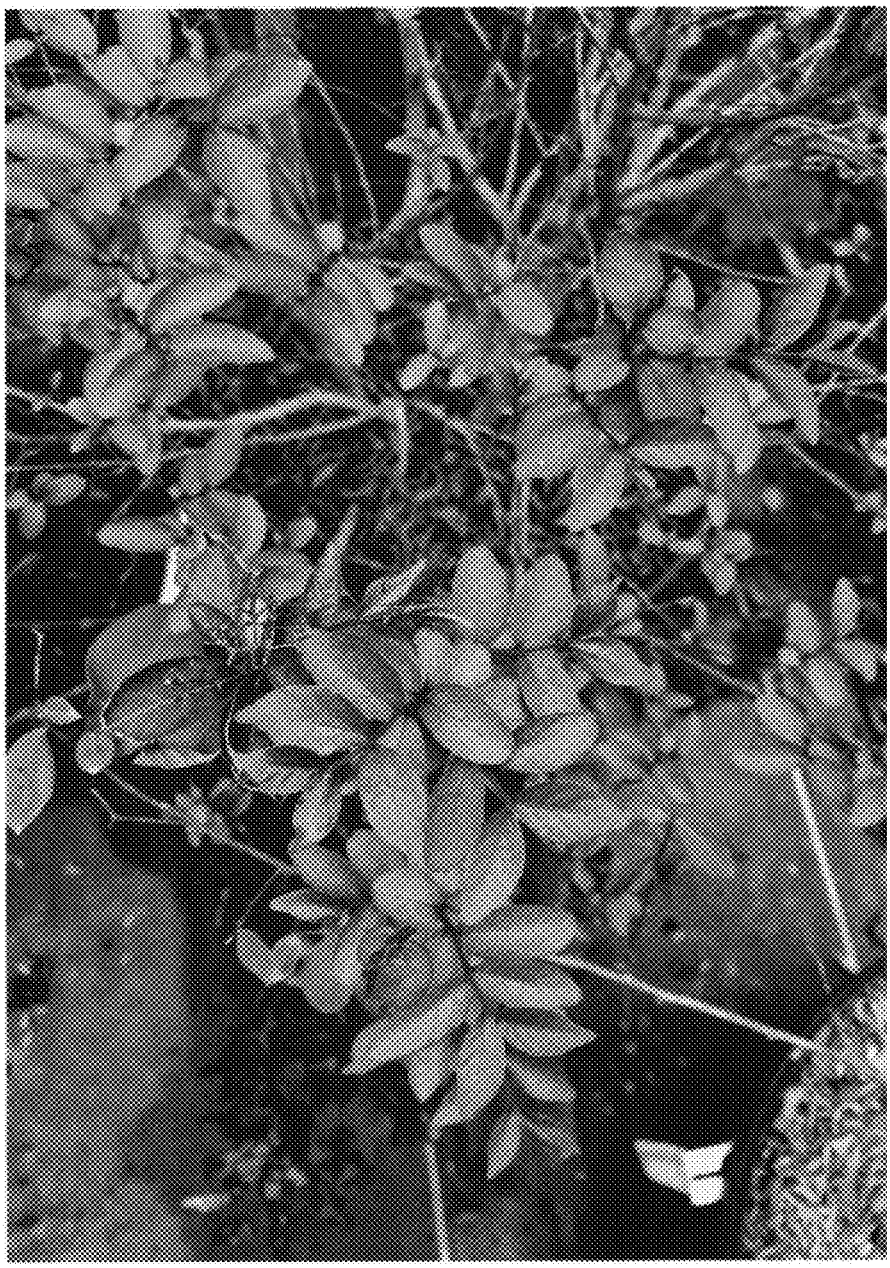
Figure 2:
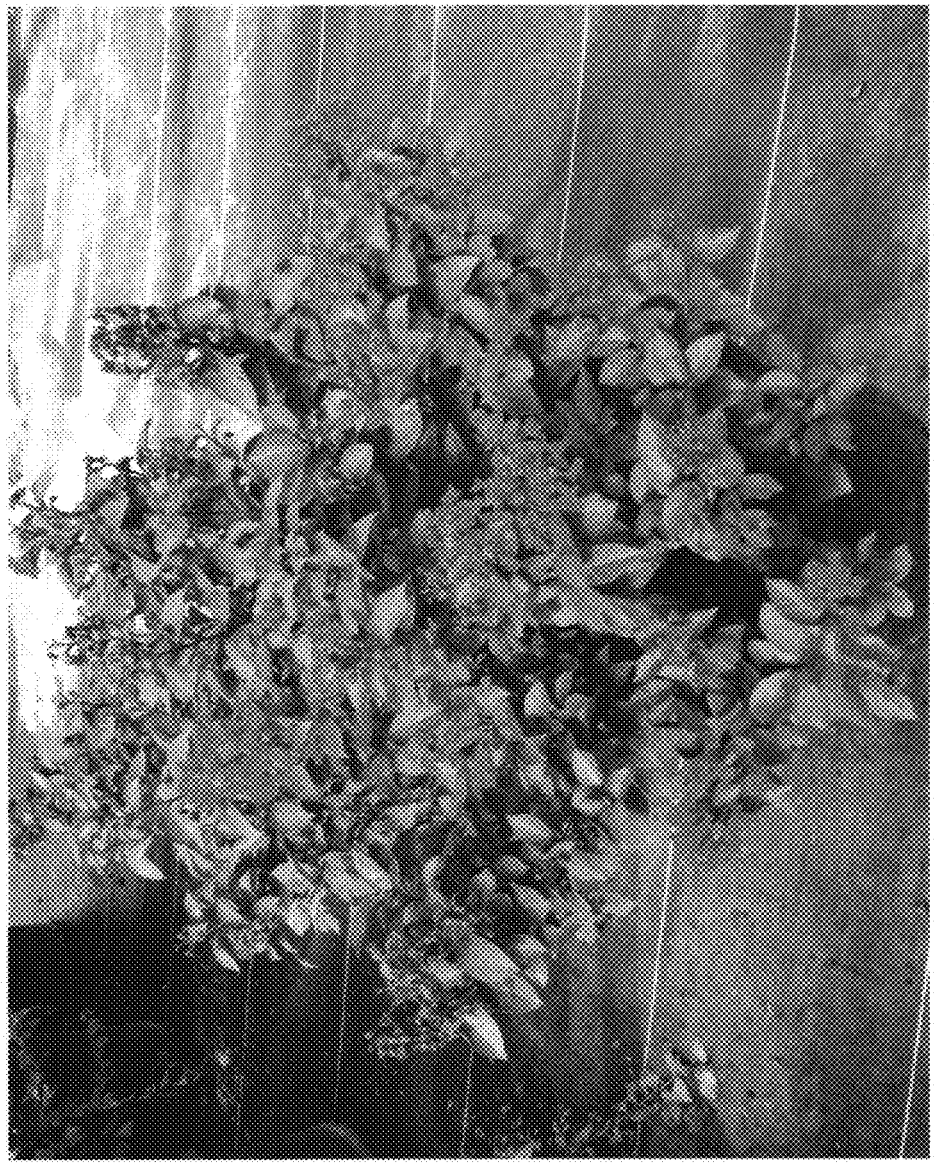
FIG. 2 illustrates a typical flowering plant of 'SMNLIMG' in a 3 gallon pot. Age of the plant photographed is approximately 2-3 years old from a rooted cutting.
Figure 3:
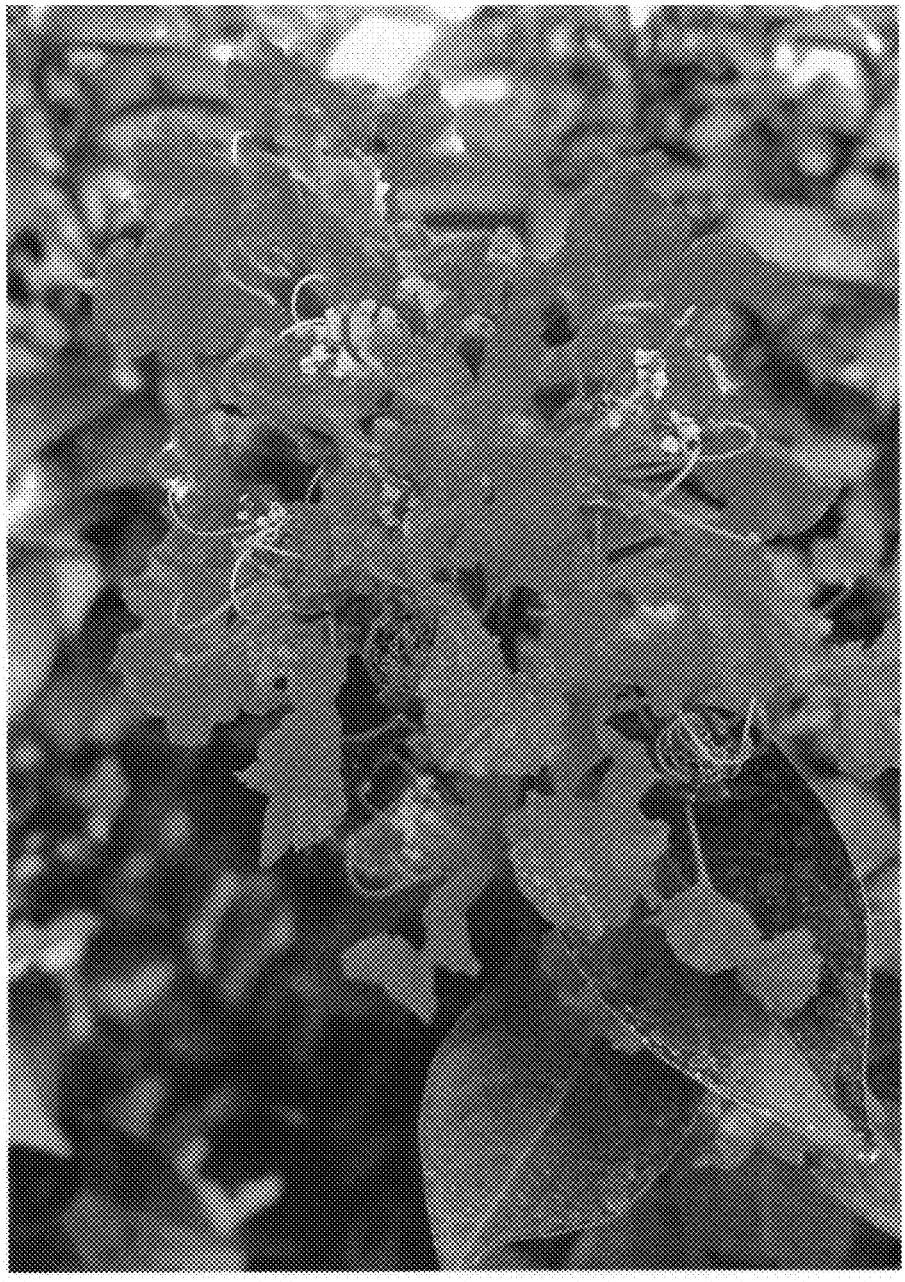
FIG. 3 illustrates a close up view of the inflorescence.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'SMNLIMG' plants grown in a poly house during August 2017, in Grand Haven, Mich. The growing temperature ranged from approximately 18° C. to 27° C. during the day and from approximately 5° C. to 10° C. during the night. General light conditions are normal sunlight and numerical values represent averages of typical plant types.

Botanical classification: *Lagerstroemia indica* 'SMNLIMG'.

PROPAGATION

Type of propagation typically used: Softwood cuttings.
Time to initiate roots: 21 days at 18-27° C.
Time to produce a rooted cutting: 1-2 months at 18-27° C.
Root description: Thin fibrous, not fleshy, freely branching. White in color, not accurately measured with R.H.S. Chart.

PLANT

Age of plant described: 2-3 years old from a rooted cutting.
Container size: 3 gallon container.
Overall plant shape: Compact, rounded.
Growth habit: Freely branching outward.
Plant spread: 70 cm.
Plant height: 58 cm.
Plant vigor: Good.
Branching habit: Basal.
Length of primary lateral branches: 41 cm.
Diameter of lateral branches: 5 mm.
Quantity of lateral branches: 30.
Stem:
- *Color*.—New growth: RHS Greyed-Purple 185C. Old growth: RHS Greyed-Brown 199A.
- *Shape*.—New growth: Square. Old growth: Round
- *Strength*.—Good.
- *Aspect angle*.—25-45°.
- *Pubescence*.—None.
- *Texture*.—New growth: Smooth. Old growth: Woody.

Internode length: 1.75 cm.

FOLIAGE

Leaf:
- *Arrangement*.—Sub-opposite.
- *Average length*.—4.2 cm.
- *Average width*.—1.8 cm.
- *Shape of blade*.—Elliptic-lanceolate.
- *Apex*.—Cuspidate.
- *Base*.—Cuneate.
- *Margin*.—Entire.
- *Texture of top surface*.—Smooth, waxy.
- *Texture of bottom surface*.—Smooth, waxy.
- *Color*.—Emerging foliage upper side: Greyed-Red 180C. Emerging foliage underside: Greyed-Purple 183D. Young foliage upper side: Blended RHS Greyed-Purple 187A and Green 143A. Young foliage under side: Blended RHS Green 143C and Greyed-Purple 183C, slightly iridescent. Mature foliage upper side: Mostly RHS Yellow-Green 146A with some Greyed-Purple 187A. Mature foliage under side: Blended RHS Green 143C and Greyed-Green 183C, slightly iridescent.
- *Venation*.—Type: Pinnate. Venation color upper side: RHS Greyed-Orange N170B. Venation color under side: RHS Greyed-Purple 185C.
- *Petiole*.—Length: 2 mm. Diameter: 1 mm. Texture, upper side: Smooth, coriaceous, slightly pubescent. Texture, under side: Smooth, coriaceous. Color, upper side: RHS Greyed-Purple N186A. Color, under side: RHS Greyed-Purple N186A.

FLOWER

Natural flowering season: Late Summer to October.
Inflorescence form: Panicle.
Flowers per inflorescence: 100.
Flowers per lateral stem: 100.
Inflorescence size:
- *Width*.—17 cm.
- *Height*.—13 cm.

Individual flowers:
- *Type*.—Rotate.
- *Habit*.—Whorled outward.
- *Diameter*.—2.5 cm.
- *Length*.—1 cm.
- *Persistence*.—Self-cleaning.
- *Fragrance*.—Lightly earthy.

Petals:
- *Arrangement*.—Whorled.
- *Number*.—6.
- *Shape*.—Orbicular.
- *Margin*.—Ruffled, undulate.
- *Tip shape*.—Rounded.
- *Base shape*.—Rounded.
- *Length*.—1 cm.
- *Width*.—8 mm.
- *Texture*.—Upper: Soft, smooth, delicate. Lower: Soft, smooth, delicate.
- *Color*.—When opening: Upper surface: RHS Red-Purple 61C. Under surface: RHS Red-Purple 61C. Fully opened: Upper surface: RHS Red-Purple 61C. Under surface: RHS Red-Purple 61C.

Bud:
- *Shape*.—Obovate.
- *Length*.—5 mm.
- *Diameter*.—6 mm.
- *Color*.—Center: RHS Greyed-Purple N186C. Outside: RHS Greyed-Purple 187B to 187C.

Sepals:
- *Appearance*.—Smooth, glossy, fused.
- *Arrangement*.—Unguiculate.
- *Shape*.—Narrowly triangular.
- *Tip shape*.—Acute.
- *Base shape*.—Obtuse.
- *Margin*.—Entire.
- *Quantity per flower*.—6.
- *Length*.—3 mm.
- *Width*.—2 mm.
- *Texture*.—Upper: Smooth, coriaceous, rugose. Lower: Smooth.

*Color*.—Upper: Mix of RHS Red-Purple 59A with Red-Purple 58B and 58C. Lower: RHS Green-White 157A.

Calyx:

*Shape*.—Unguiculate.

*Length*.—5 mm.

*Diameter*.—6 mm.

Pedicel:

*Length*.—3 mm.

*Diameter*.—1 mm.

*Texture*.—Smooth.

*Color*.—RHS Greyed-Red 182A.

*Strength*.—Good.

Peduncle: None, inflorescence begins on branch stem.

REPRODUCTIVE ORGANS

Stamens:

*Number*.—About 29.

*Filament length*.—1 cm.

*Filament color*.—RHS Red-Purple 70D, with White 155B at base.

Anthers:

*Shape*.—Linear.

*Length*.—1 mm.

*Color*.—RHS Greyed-Orange 163A edged with Greyed-Orange 165A.

*Pollen*.—Amount: Moderate. Color: RHS Greyed-Orange 163A.

Pistil:

*Number*.—1.

*Length*.—2 cm.

*Style*.—Length: 1.8 cm. Color: RHS Greyed-Purple 184D.

Stigma:

*Shape*.—Globe.

*Color*.—RHS Black 202A.

*Ovary color*.—RHS Yellow 11B.

OTHER CHARACTERISTICS

Fruits and seeds: Not observed to date.

Disease/pest resistance: Neither resistance nor susceptibility to normal diseases and pests of *Lagerstroemia* observed.

Temperature range: Observed to tolerate a temperature range from −28° C. to 35° C. Root hardy to −28 C, top of the plant does die back to the ground.

What is claimed is:

1. A new and distinct cultivar of *Lagerstroemia* plant named 'SMNLIMG' as herein illustrated and described.

* * * * *